US012446902B2

(12) United States Patent
Duffy

(10) Patent No.: US 12,446,902 B2
(45) Date of Patent: Oct. 21, 2025

(54) ASPIRATION SYSTEM INCLUDING FLUID-INFUSING INNER MEMBER

(71) Applicant: Covidien LP, Mansfield, MA (US)

(72) Inventor: Niall F. Duffy, Galway (IE)

(73) Assignee: Covidien LP, Mansfield, MA (US)

( * ) Notice: Subject to any disclaimer, the term of this patent is extended or adjusted under 35 U.S.C. 154(b) by 648 days.

(21) Appl. No.: 17/897,964

(22) Filed: Aug. 29, 2022

(65) Prior Publication Data

US 2023/0110858 A1 Apr. 13, 2023

Related U.S. Application Data

(60) Provisional application No. 63/253,679, filed on Oct. 8, 2021.

(51) Int. Cl.

| | |
|---|---|
| ***A61B 17/22*** | (2006.01) |
| ***A61M 25/00*** | (2006.01) |
| ***A61M 25/01*** | (2006.01) |

(52) U.S. Cl.

CPC ......... *A61B 17/22* (2013.01); *A61M 25/0082* (2013.01); *A61M 25/0102* (2013.01); *A61B 2017/22079* (2013.01)

(58) Field of Classification Search

CPC .............. A61B 17/22; A61B 17/32037; A61B 17/3207; A61B 2017/22079; A61B 2217/005; A61B 2217/007; A61M 25/005; A61M 25/0068; A61M 25/007; A61M 25/0082; A61M 25/0102; A61M 25/0662; A61M 2025/0004; A61M 2025/0063; A61M 2025/0681

See application file for complete search history.

(56) References Cited

U.S. PATENT DOCUMENTS 4,870,953 A 10/1989 DonMicheal et al.
5,030,201 A * 7/1991 Palestrant ...... A61B 17/320725 600/568
5,192,290 A * 3/1993 Hilal ................. A61M 25/0068 606/159

(Continued)

FOREIGN PATENT DOCUMENTS

EP 1164944 B1 7/2008
EP 3646806 A1 5/2020

(Continued)

OTHER PUBLICATIONS

International Search Report and Written Opinion of International Application No. PCT/IB2022/059623 dated Dec. 19, 2022, 15 pp.

*Primary Examiner* — Benjamin J Klein

(74) *Attorney, Agent, or Firm* — Shumaker & Sieffert, P.A.

(57) ABSTRACT

In some examples, a medical system includes an aspiration catheter defining a catheter lumen; and an inner member configured to be received in the catheter lumen and extend distally outward from a distal opening of the catheter, wherein the inner member comprises an elongated support structure configured to move axially within the catheter lumen; and a rigid member at a distal portion of the elongated support structure, wherein a proximal-facing surface of the rigid member defines one or more openings configured to deliver a fluid into vasculature of the patient to dilute or displace a volume of blood aspirated from of vasculature through the catheter lumen.

22 Claims, 7 Drawing Sheets

(56) References Cited

U.S. PATENT DOCUMENTS

| | | | | |
|---|---|---|---|---|
| 5,419,774 | A | 5/1995 | Willard et al. | |
| 5,496,267 | A | 3/1996 | Drasler et al. | |
| 6,579,298 | B1 * | 6/2003 | Bruneau | A61B 17/320758 606/159 |
| 6,958,059 | B2 | 10/2005 | Zadno-azizi | |
| 7,004,931 | B2 | 2/2006 | Hogendijk | |
| 7,033,336 | B2 | 4/2006 | Hogendijk | |
| 8,366,735 | B2 | 2/2013 | Bose et al. | |
| 8,647,294 | B2 | 2/2014 | Bonnette et al. | |
| 8,986,241 | B2 | 3/2015 | Evans et al. | |
| 9,254,144 | B2 | 2/2016 | Nguyen et al. | |
| 9,808,266 | B2 | 11/2017 | Ray et al. | |
| 11,096,712 | B2 | 8/2021 | Teigen et al. | |
| 2003/0195536 | A1 * | 10/2003 | Bashiri | A61B 17/320758 606/159 |
| 2005/0245894 | A1 | 11/2005 | Zadno-azizi | |
| 2007/0255252 | A1 | 11/2007 | Mehta | |
| 2010/0023038 | A1 | 1/2010 | Santra et al. | |
| 2018/0064526 | A1 | 3/2018 | Walzman | |
| 2018/0098778 | A1 | 4/2018 | Ogle | |
| 2018/0110533 | A1 | 4/2018 | Horak | |
| 2018/0338770 | A1 | 11/2018 | Mogi et al. | |
| 2019/0216476 | A1 | 7/2019 | Barry et al. | |
| 2020/0215300 | A1 | 7/2020 | Matsumoto | |
| 2020/0246014 | A1 | 8/2020 | Walzman | |
| 2020/0246029 | A1 | 8/2020 | Singleton et al. | |
| 2020/0289722 | A1 | 9/2020 | Culbert et al. | |
| 2020/0367917 | A1 | 11/2020 | Teigen et al. | |
| 2021/0196292 | A1 | 7/2021 | Vale | |
| 2022/0000498 | A1 * | 1/2022 | Leuthardt | A61M 25/104 |

FOREIGN PATENT DOCUMENTS

| | | | |
|---|---|---|---|
| GB | 2472213 | A | 2/2011 |
| WO | 9219161 | A1 | 11/1992 |
| WO | 2020069216 | A1 | 4/2020 |
| WO | 2021003133 | A1 | 1/2021 |

* cited by examiner

ASPIRATION SYSTEM INCLUDING FLUID-INFUSING INNER MEMBER

This application claims the benefit of U.S. Provisional Patent Application No. 63/253,679, filed on Oct. 8, 2021, and entitled, "ASPIRATION SYSTEM INCLUDING FLUID-INFUSING INNER MEMBER," the entire content of which is incorporated herein by reference.

TECHNICAL FIELD

This disclosure relates to medical devices.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels.

SUMMARY

This disclosure describes example aspiration systems that include an inner member configured to fit within an aspiration catheter lumen and disrupt and/or penetrate a thrombus positioned within vasculature of a patient. The inner member is further configured to direct a flow of fluid, such as saline, in a generally proximal direction, which may provide one or more benefits, as detailed below. The inner member includes an elongated support structure and a substantially rigid or noncompliant member at a distal portion thereof, which is configured to fit within the aspiration catheter lumen. The rigid member defines a larger cross-sectional dimension than the elongated support structure, and may be deployed distally outward from the aspiration catheter lumen via a distal opening of the catheter to contact and disrupt (e.g., break-up or segment) the thrombus. In some examples, the rigid member may be alternatingly distally deployed and proximally withdrawn to repeatedly contact and segment the thrombus. A suction force may be applied to the catheter lumen to aspirate the segmented thrombus portions into the distal opening of the catheter for removal from the vasculature.

While the rigid member of the inner member is deployed distally outward from the distal opening of the catheter, a clinician may direct a flow of a fluid, such as saline, from a plurality of openings defined by a proximal-facing surface of the rigid member, which may help direct portions of the thrombus into the distal opening of the catheter. In some examples, the proximally directed fluid flow delivered via the inner member is configured to dilute and/or displace a volume of incidental patient fluid, such as blood, that might otherwise be withdrawn from the patient through the catheter lumen during the aspiration procedure. When the rigid member is proximally retracted back into the catheter lumen, the clinician may direct the flow of the fluid from the plurality of openings and proximally through the catheter lumen to flush the lumen of the catheter. Enabling flushing of the catheter without removal of the catheter from the patient may help limit the time required to complete a medical aspiration catheter.

In some examples, the inner member includes an elongated distal tip, e.g., a guidewire, configured to enable the inner member to penetrate through the thrombus.

In some examples, a medical system that includes an example of the catheters and inner member described above may further include a suction source, a fluid source, and a controllable valve or switch fluidically coupled to the suction source and/or the fluid source. Control circuitry is configured to control the valve to enable control over (e.g., to synchronize) a volume of fluid introduced via the inner member, a volume of aspirated patient fluid, or both volumes relative to one another. This disclosure also describes examples of methods of forming the catheters described herein and methods of using the catheters. The examples described herein may be combined in any permutation or combination.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
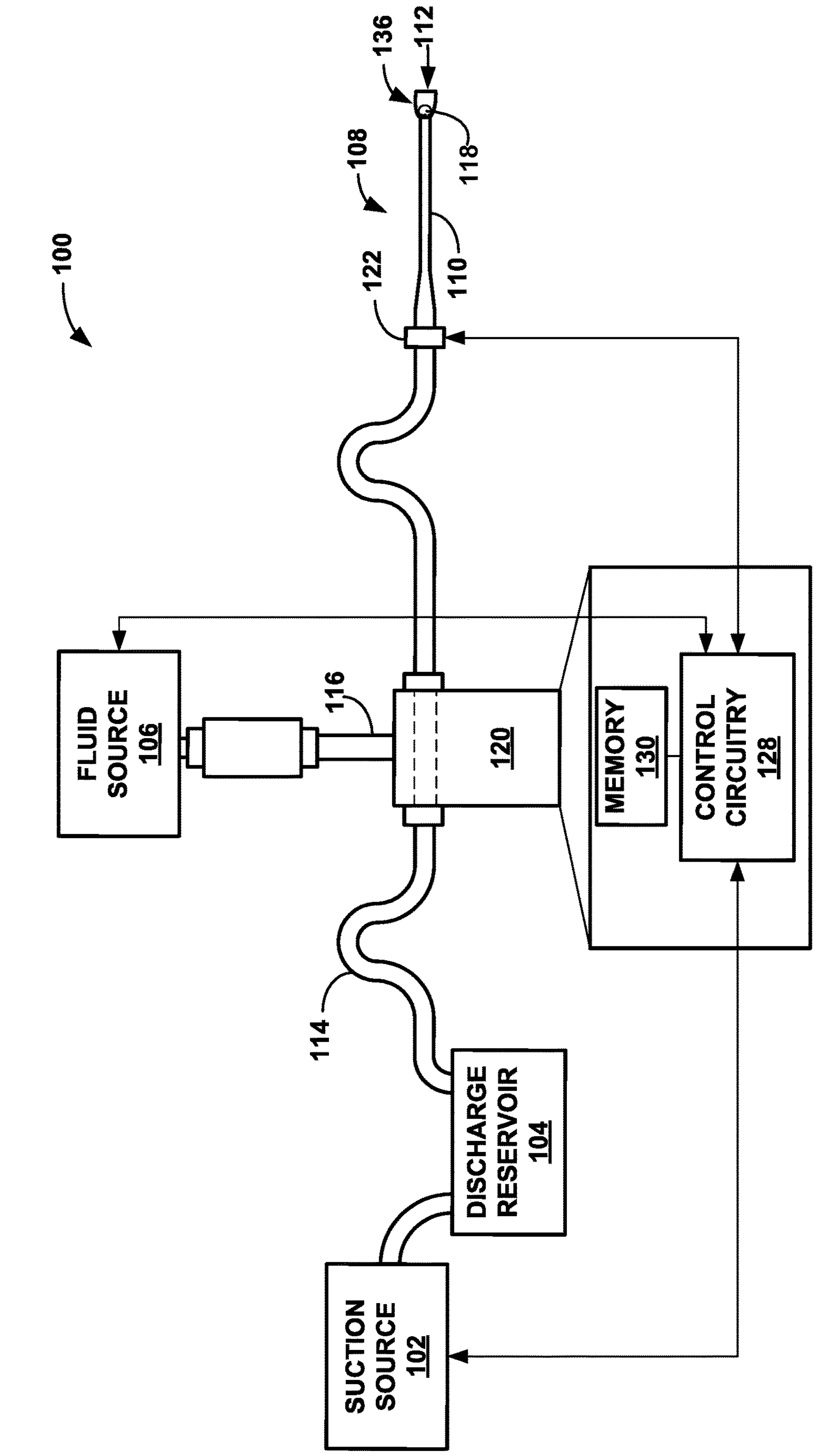
FIG. 1 is a schematic diagram illustrating an example medical aspiration system.

The disclosure describes example aspiration system includes an aspiration catheter and a longitudinally deployable inner member configured to engage with a thrombus (e.g., a blood clot or other material such as a plaques or foreign bodies) positioned within vasculature of a patient, in order to facilitate aspiration and removal of the thrombus from the vasculature. The inner member is configured to move axially (e.g., proximally and distally) relative to the flexible elongated body of the aspiration catheter (also referred to herein more generally as a catheter) in order to disrupt and/or penetrate the thrombus. Disruption of the thrombus by the inner member may compress the thrombus into a smaller volume or break the thrombus up into smaller segments, which may facilitate aspiration of the thrombus through a lumen of the aspiration catheter (referred to herein as a catheter lumen or an aspiration catheter lumen). In addition, the inner member is configured to direct a flow of fluid, such as saline, in a generally proximal direction, to dilute and/or displace a volume of incidental patient fluid, such as blood, that might otherwise be withdrawn from the patient through the catheter lumen during the aspiration procedure. The fluid may also help direct the thrombus towards the catheter lumen.

Medical aspiration may be used to treat a variety of conditions, including thrombosis. Thrombosis occurs when a thrombus (e.g., a blood clot or other embolus) forms and obstructs vasculature of a patient. To treat a patient with thrombosis, a clinician may position an aspiration catheter in a blood vessel of the patient near the thrombus or other occlusion, and apply a suction force to the catheter to engage the thrombus with suction force at a tip of the catheter. Once the tip of the aspiration catheter has engaged the thrombus, the clinician may remove the aspiration catheter with the thrombus attached to the tip or suction off pieces of the thrombus (or the thrombus as a whole) until the thrombus is removed from the blood vessel of the patient through a lumen of the aspiration catheter itself and/or through the lumen of an outer catheter in which the aspiration catheter is at least partially positioned.

The suction force can be generated by any suitable mechanism, such as a vacuum, e.g., by creating a partial vacuum using a vacuum pump, or by direct displacement of fluid in a catheter or tubing via a peristaltic pump. The suction force includes concepts such as suction pressure, vacuum force, vacuum pressure, negative pressure, and the like.

It may be desirable to limit blood loss during a medical aspiration procedure. If the distal tip of the catheter is not fully engaged with a thrombus as a suction force is being applied to a lumen of the catheter, then blood may be unintentionally aspirated from the patient via the catheter. The aspiration systems described herein include an aspiration catheter and an inner member configured to help reduce an amount of blood aspirated from a vasculature of a patient to limit blood loss during a medical aspiration procedure. For example, as described in further detail below, the inner member can be configured to mechanically engage with a thrombus to reduce an amount of time required to aspirate the thrombus from the vasculature. As another example, as described in further detail below, the inner member is configured to deliver a fluid in a proximal direction, towards the aspiration catheter, to help displace or dilute blood that is aspirated through the catheter lumen.

Some thrombi, such as thrombi that have been present in the thrombus for a relatively long period of time, may be relative dense and difficult to aspirate through the catheter lumen in an efficient manner. The inner member described herein is configured to help configure the thrombus to facilitate the aspiration, such as by mechanically breaking up the thrombus into smaller pieces and/or by compressing the thrombus or pieces of the thrombus into a smaller volume. This may help shorten the time required to aspirate the thrombus from the patient, as well as reduce the time suction force is applied to the catheter lumen, which may reduce an amount of blood that is incidentally removed from the vasculature through the catheter lumen during the aspiration procedure.

In some examples, the inner member includes an elongated structure and a rigid member at a distal portion thereof. The rigid member has a maximum cross-sectional dimension (e.g., a diameter) that is larger than the maximum cross-sectional dimension (e.g., diameter) of the elongated structure, so that it can be considered enlarged relative to the elongated structure, where the cross-sections are taken in a direction orthogonal to a longitudinal axis of the elongated structure. The rigid member is configured to substantially maintain its size and shape, e.g., is not configured to expand or inflate during the aspiration procedure and may not be noncompliant (e.g., may not readily conform to walls of the vasculature). The rigid member may be deployed distally outward from a distal opening of the catheter to contact and disrupt the thrombus. In some examples, the rigid member may be alternatingly distally deployed and proximally withdrawn, e.g., according to a controllable frequency, to repeatedly contact and segment the thrombus. A suction force may be applied to aspirate the segmented thrombus portions into the distal opening of the catheter for removal from the patient's vasculature.

The rigid member of the inner member further includes a proximal-facing surface defining a plurality of openings fluidically coupled to a lumen of the inner member. In some examples, the rigid member of the inner member includes a distal tip configured to facilitate penetration of the rigid member through the thrombus toward a distal side of the thrombus. For example, the distal tip can include an elongated element, e.g., a guidewire, which can be tapered in a distal direction in some examples. While the inner member is in this deployed configuration on the distal side of the thrombus, a clinician may direct a flow of a fluid, such as saline, from the plurality of openings on the proximal-facing surface of the rigid member to help direct segmented portions of the thrombus into the catheter lumen via the distal opening of the catheter. Additionally or alternatively, when the inner member is subsequently retracted back into the distal opening of the catheter, the proximal fluid flow may be introduced within the catheter lumen to help flush the catheter lumen, e.g., clear the catheter lumen of material (e.g., a thrombus) that may be blocking fluid flow through the lumen.

For either application, the proximally directed fluid flow is configured to dilute and/or displace a volume of incidental patient fluid, such as blood, that might otherwise be withdrawn from the patient during the aspiration procedure. As detailed further below, in some examples, a medical system that includes the aspiration catheter and inner member includes control circuitry configured to control a volume of fluid introduced via the inner member, a volume of patient fluid aspirated via the catheter, or both fluid volumes according to desired amounts relative to one another.

FIG. 1 is a schematic diagram illustrating an example medical system 100 including a suction source 102, a discharge reservoir 104, a fluid source 106, an aspiration catheter 108, and an inner member 118 configured to be received in a lumen of catheter 108. Medical system 100 may be used to treat a variety of conditions, including thrombosis. Thrombosis occurs when a thrombus (e.g., a blood clot or other material such as plaques or foreign bodies) forms and obstructs vasculature of a patient. For example, medical system 100 may be used to treat deep vein thrombosis.

Medical system 100 is configured to remove fluid via catheter 108, e.g., draw fluid from catheter 108 into discharge reservoir 104, via a suction force applied by suction source 102 to catheter 108 (e.g., to a catheter lumen of catheter 108). As detailed further below, catheter 108 includes a flexible elongated body 110 defining a catheter lumen (not shown in FIG. 1) and defining a distal opening 112 to the catheter lumen. To treat a patient with thrombosis, a clinician may position distal opening 112 in a blood vessel of the patient near the thrombus or other occlusion, and apply a suction force (also referred to herein as suction, vacuum force, or negative pressure) to catheter 108 (e.g., to one or more lumens of the catheter) to engage the thrombus with suction force at distal opening 112. For example, suction source 102 can be configured to create a negative pressure within the catheter lumen of catheter 108 to draw a fluid, such as blood, an aspiration fluid, more solid material, or a combination thereof, into the catheter lumen via distal opening 112 of catheter 108. The negative pressure within the catheter lumen can create a pressure differential between the catheter lumen and the environment external to at least a distal portion of catheter 108 that causes fluid and other material to be introduced into the catheter lumen via distal opening 112. For example, the fluid may flow from patient vasculature, into the catheter lumen via distal opening 112, and subsequently through aspiration tubing 114 (also referred to herein as "vacuum tube 114") into discharge reservoir 104.

Once distal opening 112 of aspiration catheter 108 has engaged the thrombus, the clinician may remove aspiration catheter 108 with the thrombus held within distal opening 112 (or appended to a distal-most end of elongated body 110 that defines distal opening 112), or suction off pieces of the thrombus (or the thrombus as a whole) until the thrombus is removed from the blood vessel of the patient, either through the catheter lumen of aspiration catheter 108 itself, and/or through the lumen of an outer catheter (or "sheath") in which aspiration catheter 108 is at least partially positioned. The outer catheter can be, for example, a guide catheter configured to provide additional structural support to aspiration catheter 108.

As detailed further below with respect to FIGS. 3-6, aspiration of a thrombus with an aspiration force can be performed concurrently with use of a longitudinally deployable inner member 118. Inner member 118 includes an elongated support structure and a rigid (e.g., non-expandable, non-inflatable, and/or non-deformable) member configured to move proximally and distally (relative to elongated catheter body 110) to forcefully contact and disrupt a portion of a thrombus to facilitate aspiration of the thrombus into the catheter lumen via distal opening 112. The disruption can include, for example, breaking the thrombus into smaller segments and/or compressing the thrombus into a smaller volume. Additionally, the rigid distal portion of inner member 118 defines a plurality of openings configured to deliver a fluid into vasculature of a patient during the aspiration procedure, where the fluid is configured to flow in a proximal direction (e.g., towards distal opening 112 when inner member 118 is deployed from the catheter lumen) against segmented thrombus portions to direct the thrombus portions into and/or through the catheter lumen.

For instance, in some examples, aspiration system 100 is configured to deliver fluid from fluid source 106, for example, a fluid reservoir different from discharge reservoir 104, through irrigation tubing 116 (also referred to herein as "irrigation tube 116" or "flush tube 116") and into a lumen of inner member 118 for controlled deployment of the fluid.

As used herein, "suction force" is intended to include, within its scope, related concepts such as suction pressure, vacuum force, vacuum pressure, negative pressure, fluid flow rate, and the like. A suction force can be generated by a vacuum, e.g., by creating a partial vacuum within a sealed volume fluidically connected to a catheter, or by direct displacement of liquid in a catheter or tubing via (e.g.) a peristaltic pump, or otherwise. Accordingly, suction forces or suction as specified herein can be measured, estimated, computed, etc. without need for direct sensing or measurement of force. A "higher," "greater," or "larger" (or "lower," "lesser," or "smaller") suction force described herein may refer to the absolute value of the negative pressure generated by the suction source on catheter 108 or another component, such as discharge reservoir 104.

In some examples, suction source 102 can comprise a pump (also referred to herein as "pump 102" or "vacuum source 102"). The suction source 102 can include one or more of a positive displacement pump (e.g., a peristaltic pump, a rotary pump, a reciprocating pump, or a linear pump), a direct-displacement pump (e.g., a peristaltic pump, or a lobe, vane, gear, or piston pump, or other suitable pumps of this type), a direct-acting pump (which acts directly on a liquid to be displaced or a tube containing the liquid), an indirect-acting pump (which acts indirectly on the liquid to be displaced), a centrifugal pump, and the like. An indirect-acting pump can comprise a vacuum pump, which displaces a compressible fluid (e.g., a gas such as air) from the evacuation volume (e.g., discharge reservoir 104, which can comprise a canister), generating suction force on the liquid. Accordingly, the evacuation volume (when present) can be considered part of the suction source. In some examples, suction source 102 includes a motor-driven pump, while in other examples, suction source 102 can include a syringe configured to be controlled by control circuitry 128, and mechanical elements such as linear actuators, stepper motors, and the like. As further examples, the suction source 102 could comprise a water aspiration venturi or ejector jet.

Control of suction source 102 can comprise control, operation, and the like, of any one or combination of the component(s) making up the suction source. Accordingly, in examples in which suction source 102 includes a pump and an evacuation volume, control of the suction source can comprise control of only the pump, of only the evacuation volume, or of both of those components. As in examples in which suction source 102 includes only a pump, control of suction source 102 comprises control of the pump.

In some examples, an operator of aspiration system 100 may introduce an aspiration/irrigating fluid, such as saline, from a fluid reservoir 106 via tube 116 and an inner lumen of inner member 118 (e.g., while inner member 118 is positioned within the catheter lumen) to flush and/or prime the lumen of catheter 108 (e.g., an infusion state), or to deliver fluid for aspirating back into discharge reservoir 104 to help reduce the amount of blood that is aspirated from the patient during an aspiration procedure. System 100 can be configured to deliver the fluid to an inner lumen of inner member 118 and not directly into catheter lumen of catheter 108. While this fluid may eventually be withdrawn back into the catheter lumen, the fluid is not directly introduced into the catheter lumen. The operator can also operate suction source 102 to draw material (e.g., a thrombus, saline or other fluid in fluid source 160) from a site of distal opening 112 of aspiration catheter 108 via vacuum tube 114, into discharge reservoir 104.

Aspiration system 100 includes control circuitry 128 configured to control a suction force applied by suction source 102 to the catheter lumen. For example, control circuitry 128 can be configured to directly control an operation of suction source 102 to vary the suction force applied by suction source 102 to the lumen of catheter 108, e.g. by controlling the motor speed, or stroke length, volume or frequency, or other operating parameters, of suction source 102. For instance, control circuitry 128 may vary the suction force by intermittently varying the aspiration force, by periodically varying the aspiration force, or by pulsing the aspiration force, as a few non-limiting examples.

As another example, control circuitry 128 can be configured to control communication of an aspiration fluid, such as saline, from fluid source 106 to the lumen of inner member 118. For instance, medical system 100 may include an electronic valve 120 coupled to aspiration tubing 114, irrigation tubing 116, or both. Control circuitry 128 may be operatively coupled to valve 120 to convert valve 120 between an "open" configuration and a "closed" configuration to promote or inhibit, respectively, a fluid flow through the tubing to which the valve 120 is coupled. In some such examples, medical system 100 includes a user-input mechanism enabling a user to select an amount of aspiration fluid introduced into the lumen of inner member 118 via fluid source 106 (e.g., by controlling a valve 120 coupled to irrigation tubing 116). Additionally or alternatively, the user-input mechanism may enable the user to select an amount of fluid (including patient fluid, aspiration fluid, and/or more-viscous material, as described above) aspirated into discharge reservoir 104 (e.g., by controlling a valve 120 coupled to aspiration tubing 114). In either example, the user interface may be configured such that the respective amount of fluid may be selected or indicated in the form of a fixed amount (e.g., a measurable fluid volume), a fixed rate (e.g., a flow rate), a relative amount (e.g., a volume of "introduced" fluid relative to a volume of "aspirated" fluid, or vice versa), or a relative rate (e.g., a flow rate of introduced fluid relative to a flow rate of aspirated fluid, or vice versa).

In some examples, inner member 118 includes a proximal actuator mechanism (e.g., a switch, slider, etc.) enabling a user, such as a clinician, to manually translate inner member 118 in proximal and distal directions relative to catheter 108. Additionally or alternatively, control circuitry 128 can be configured to control a longitudinal movement of inner member 118, e.g., according to a predetermined motion pattern to contact, segment, and/or penetrate a portion of a thrombus that is aspirated into the catheter lumen. For instance, control circuitry 128 may be configured to actuate a longitudinal motion, a rotational motion, a motion in a direction transverse to longitudinal axis 150, and/or an oscillating motion of inner member 118 within the catheter lumen of catheter 108. Control circuitry 128 may actuate the motion of inner member 118 through any suitable motion mechanism 122, such as via a rotating cam, or via linear or rotary actuator(s) which can be electrically, electromagnetically, pneumatically or hydraulically driven to generate the desired movement of inner member 118. Such linear or rotary actuator(s) can be linear solenoid(s), rotary solenoid(s), or piezoelectric driven linear or rotary actuator(s). Regardless of the type of driving mechanism or actuator, control circuitry 128 may cause the motion mechanism 122 to actuate the motion of inner member 118 according to a single proximal or distal motion (e.g., a single motion per received user input), according to a predetermined speed or frequency, and/or according to a variable speed or frequency within a predetermined range of speeds or frequencies. As a non-limiting example, control circuitry 128 may cause inner member 118 to oscillate or otherwise periodically move at a frequency from about 5000 Hertz (Hz) to about 50,000 Hz.

Control circuitry 128, as well as other processors, processing circuitry, controllers, control circuitry, and the like, described herein, may include any combination of integrated circuitry, discrete logic circuity, analog circuitry, such as one or more microprocessors, digital signal processors (DSPs), application specific integrated circuits (ASICs), or field-programmable gate arrays (FPGAs). In some examples, control circuitry 128 may include multiple components, such as any combination of one or more microprocessors, one or more DSPs, one or more ASICs, or one or more FPGAs, as well as other discrete or integrated logic circuitry, and/or analog circuitry. In some examples, control circuitry 128 is or includes a "smart" device or system, including, but not limited to, a robotic device (e.g., a robotic surgical system), a device configured to operate with the aid of artificial intelligence (AI), a virtual reality (VR) system configured to aid a clinician with the medical procedure, cloud-based interfaces for data processing and/or data storage, or any combination thereof In some examples, control circuitry 128 may further include, additionally or alternatively to electric-based processors, one or more controls that operate using fluid motion power (e.g., hydraulic power) in combination with or in addition to electricity. For example, control circuitry 128 can include a fluid circuit comprising a plurality of fluid passages and switches arranged and configured such that, when a fluid (e.g., a liquid or gas) flows through the passages and interacts with the switches, the fluid circuit performs the functionality of control circuitry 128 described herein.

Memory 130 may store program instructions, such as software, which may include one or more program modules, which are executable by control circuitry 128. When executed by control circuitry 128, such program instructions may cause control circuitry 128 to provide the functionality ascribed to control circuitry 128 herein. The program instructions may be embodied in software and/or firmware. Memory 130, as well as other memories described herein, may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

In the example shown in FIG. 1, control circuitry 128 is configured to control an amount of suction force applied by suction source 102 to the catheter lumen of catheter 108. In some examples, suction source 102 is configured to apply a substantially continuous suction force (e.g., continuous or nearly continuous to the extent permitted by the hardware) to discharge reservoir 104, and the amount of this suction force that is transferred to the catheter lumen of catheter 108 may be adjusted by control circuitry 128. As used herein, a "continuous" suction force may include a suction force having a relative strength that is generally constant over time, or that varies in strength such that distal opening 112 experiences a constant pressure and/or a constant change in pressure to help pull thrombus portions into the catheter lumen.

In some examples, but not all examples, a distal portion of elongated body 110 of catheter 108 includes an expandable distal portion 136 configured to expand radially outward to widen distal opening 112 for engaging with a thrombus.

Figure 2:
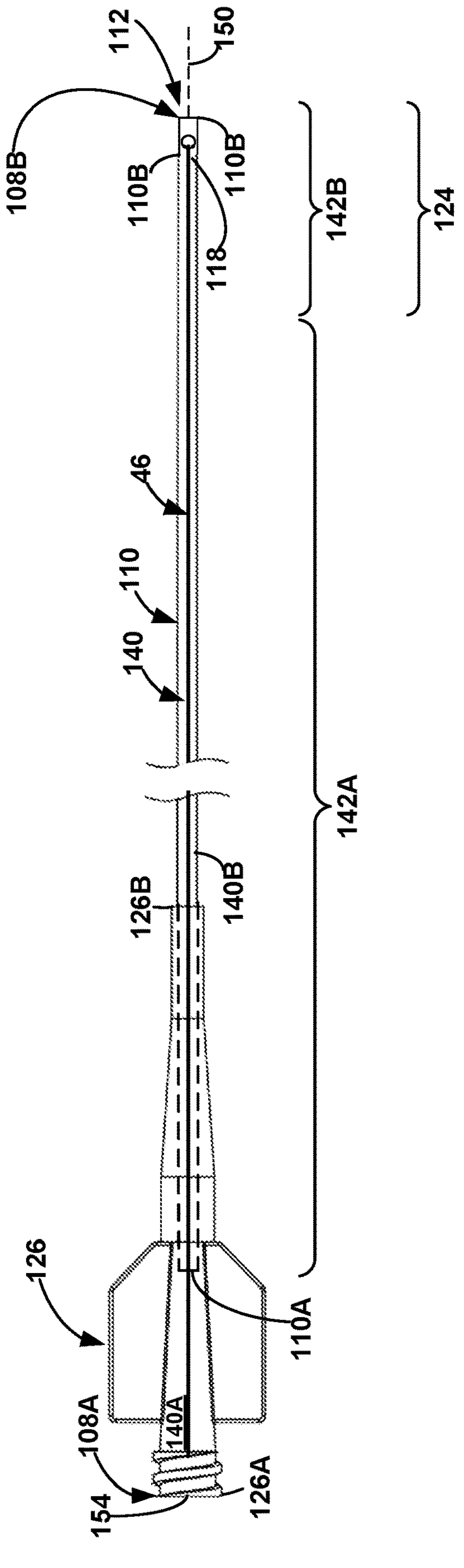
FIG. 2 is a conceptual side view of an example catheter of the medical aspiration system of FIG. 1, which includes an aspiration catheter and an inner member.
Figure 3:
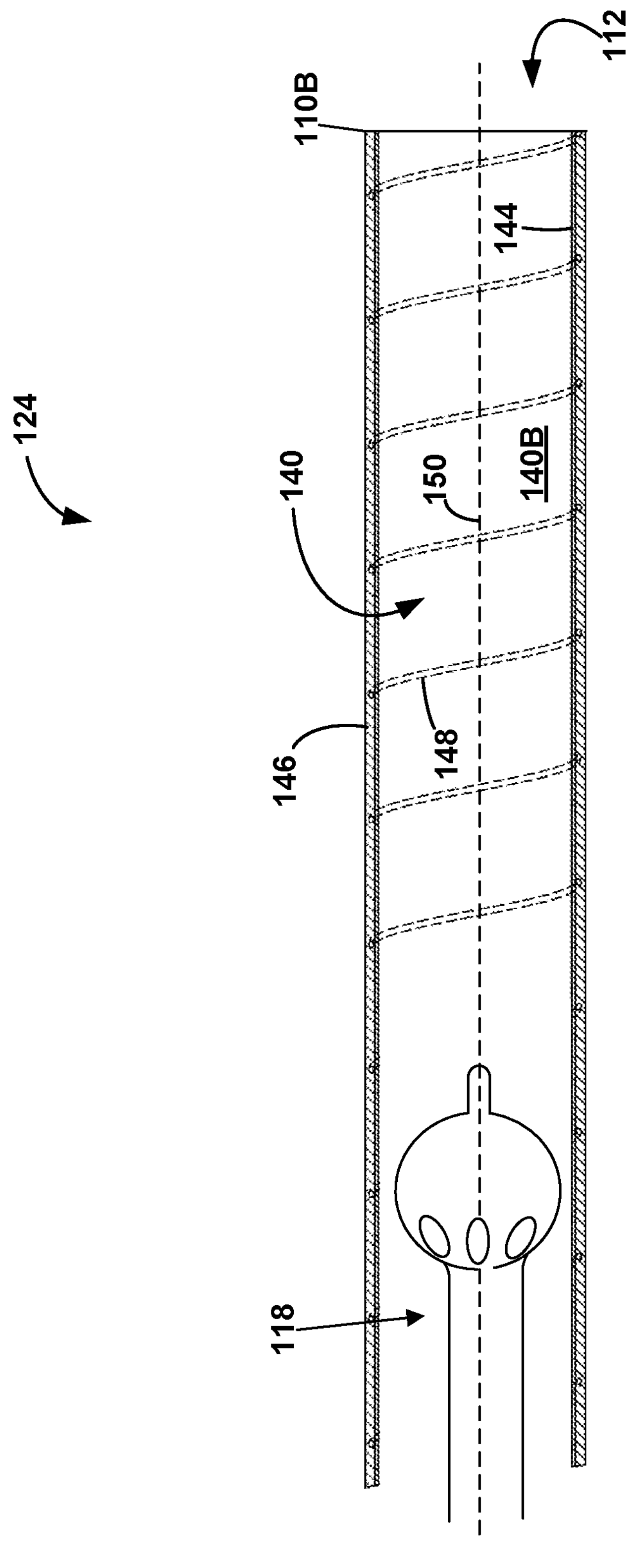
FIG. 3 is a conceptual cross-sectional view of an example distal portion of the catheter of FIG. 2, including the inner member, where the cross-section is taken through a center of the catheter and along a longitudinal axis of the catheter.

FIG. 2 is a conceptual side view of an example of aspiration catheter 108 and inner member 118 of medical system 100 of FIG. 1, and FIG. 3 is a conceptual cross-sectional view of a distal portion 124 of the example catheter 108 and inner member 118. As shown in FIGS. 2 and 3, catheter 108 can include an elongated body 110, a hub 126. Catheter 108 defines a catheter lumen 140, including a hub lumen 140A and a body lumen 140B. Catheter 108 does not include expandable distal portion 136 in the example shown in FIG. 2.

Elongated body 110 is configured to be advanced through vasculature of a patient via a pushing force applied to proximal body portion 142A (e.g., via hub 126) of elongated body 110 without buckling, kinking, or otherwise undesirably deforming (e.g., ovalization). Elongated body 110 may be structurally configured to be relatively flexible, pushable, and relatively kink- and buckle-resistant, so that it may resist buckling when a pushing force is applied to a relatively proximal section of catheter 108 (e.g., via hub 126) to advance elongated body 110 distally through vasculature, and so that it may resist kinking when traversing around a tight turn in the vasculature. In some examples, elongated body 110 is configured to substantially conform to the curvature of the vasculature. Catheter 108 may be used to access tissue sites throughout the coronary and peripheral vasculature, the cranial vasculature, the gastrointestinal tract, the urethra, ureters, fallopian tubes, veins and other hollow anatomical structures of a patient.

As shown in FIG. 3, elongated body 110 can include a plurality of concentric layers, such as an inner liner 144, an outer jacket 146, and a structural support member 148 (e.g., a coil, braid, and/or hypotube) positioned between inner liner 144 and outer jacket 146. For example, structural support member 148 can be positioned between inner liner 144 and outer jacket 146 along a full length of inner liner 144 and/or outer jacket 146 or only along part of the length. Elongated body 110 includes a proximal body portion 142A and a distal body portion 142B, which are each longitudinal sections of elongated body 110. Elongated body 110 extends from body proximal end 110A to body distal end 110B and defines at least one body lumen 140B (also referred to as a body inner lumen). In the example shown in FIG. 2, proximal end 110A of elongated body 110 is received within a distal portion of hub 126 and is mechanically connected to hub 126 via an adhesive, welding, or another suitable technique or combination of techniques. Catheter lumen 140 of catheter 108 may be defined by portions of hub 126 and inner liner 144.

Catheter 108 may be used as an aspiration catheter to remove a thrombus or other material such as plaques or foreign bodies from vasculature of a patient. In such examples, a suction force (e.g., a vacuum) may be applied to proximal end 108A of catheter 108 (e.g., via hub 126) to draw a thrombus or other blockage into catheter lumen 140.

Hub 126 may be positioned at (e.g., proximal to or at least partially overlapping with) a proximal body portion 142A of elongated body 110. Proximal end 126A of hub 126 may define catheter proximal end 108A of catheter 108 and may include a proximal opening 154 aligned with body lumen 140B of elongated body 110, such that body lumen 140B of elongated body 110 may be accessed via proximal opening 154 and, in some examples, closed via proximal opening 154. For example, hub 126 may include a luer connector, a valve, such as a hemostasis valve, or another mechanism or combination of mechanisms for connecting hub 126 to another device such as vacuum source 102 (FIG. 1) for performing the aspiration techniques described herein. In some examples, proximal end 108A of catheter 108 can include another structure in addition to, or instead of, hub 126.

In some examples, inner liner 144 of elongated body 110 defines at least a portion (e.g., body lumen 140B) of catheter lumen 140 of catheter 108, body lumen 140B defining a fluid passageway through elongated body 110. In some examples, body lumen 140B may extend over the entire length of inner liner 144 (e.g., from proximal end 110A of elongated body 110 to distal end 110B). Body lumen 140B may be sized to receive a medical device (e.g., another catheter, a guidewire, an embolic protection device, a stent, inner member 118, a mechanical thrombectomy device, or any combination thereof), a therapeutic agent, or the like. Elongated body 110, alone or with inner liner 144 and/or other structures, may define a single catheter lumen 140, or multiple catheter lumens (e.g., two catheter lumens or three catheter lumens) of catheter 108.

Body lumen 140B formed at least by inner liner 144 may define an inner diameter of elongated body 110. The diameter of body lumen 140B (as measured in a direction perpendicular to a longitudinal axis 150 of elongated body 110) may vary based on the one or more medical procedures with which catheter 108 may be used. In some examples, the diameter of body lumen 140B of elongated body 110 may be substantially constant (e.g., constant or nearly constant) from proximal end 110A to distal end 110B or may taper (gradually or more step-wise) from a first inner diameter at proximal end 110A to a second, smaller inner diameter just proximal to distal opening 112.

Inner liner 144 may be formed using any suitable material, such as, but not limited to, polytetrafluoroethylene (PTFE), expanded PTFE (ePTFE, e.g., unidirectional ePTFE or bi-directional ePTFE), a fluoropolymer, perfluoroalkyoxy alkane (PFA), fluorinated ethylene propylene (FEP), polyolefin elastomers, Low Density Polyethylene (LDPE) (e.g., about 42D), High Density Polyethylene (HDPE), or any combination thereof.

In some examples, one or more portions of the inner surface of inner liner 144 defining body lumen 140B may be lubricious to facilitate the introduction and passage of a medical device (e.g., another catheter, inner member 118, a guide member, an embolic protection device, a stent, a thrombectomy device, or any combination thereof), a therapeutic agent, a thrombus, or the like, through lumen 140B.

Elongated body 110 includes one or more structural support members 148 positioned over inner liner 144. Structural support member 148 is configured to increase the structural integrity of elongated body 110 while allowing elongated body 110 to remain relatively flexible. For example, structural support member 148 may be configured to help elongated body 110 substantially maintain its cross-sectional shape (e.g., circular or nearly circular) or at least help prevent elongated body 110 from buckling or kinking as it is navigated through tortuous anatomy. Additionally, or alternatively, structural support member 148, together with inner liner 144, and outer jacket 146, may help distribute both pushing and rotational forces along a length of elongated body 110, which may help prevent kinking of elongated body 110 upon rotation of body 110 or help prevent buckling of body 110 upon application of a pushing force to body 110. As a result, a clinician may apply pushing forces, rotational forces, or both, to the proximal portion of elongated body 110, and such forces may cause a distal portion of elongated body 110 to advance distally, rotate, or both, respectively.

Structural support member 148 includes a tubular body, such as a relatively thin-walled tube, which may include one or more tubular braided structures, one or more coil members defining a plurality of turns, e.g., in the shape of a helix, one or more hypotubes, or a combination of one or more braided structures, one or more coil members, and/or one or more hypotubes. Thus, although the examples of the disclosure primarily describe structural support member 148 as a coil, in other examples, catheter 108 may include a braided structure instead of a coil, a braided structure in addition to a coil, or a combination that includes one or more of each structure. As one example, a proximal portion of structural support member 148 may include a braided structure and a distal portion of structural support member 148 may include a coil member.

Structural support member 148 can be made from any suitable material, such as, but not limited to, a metal (e.g., a nickel titanium alloy (Nitinol), stainless steel, tungsten, titanium, gold, platinum, palladium, tantalum, silver, or a nickel-chromium alloy, a cobalt-chromium alloy, or the like), a polymer, a fiber, or any combination thereof. In some examples, structural support member 148 may include one or more metal wires braided or coiled around inner liner 144.

The metal wires may include round wires, flat-round wires, flat wires, or any combination thereof In some examples, structural support member 148 may be coupled, adhered, or mechanically connected to at least a portion of an outer surface of inner liner 144. For example, structural support member 148 may be positioned over inner liner 144 and secured in place (e.g., fixed) relative to inner liner 144 by outer jacket 146 using a melt-reflow/heat shrink process, via adhesives or other suitable technique. Additionally or alternatively, structural support member 148 may be secured to inner liner 144 with the assistance of a support layer (not shown) that helps adhere structural support member 148 to one or both of inner liner 144 and outer jacket 146. The support layer may include a thermoplastic material or a thermoset material, such as a thermoset polymer or a thermoset adhesive that bonds to inner liner 144, outer jacket 146, or both.

In the example shown in FIG. 3, outer jacket 146 is positioned over structural support member 148 and inner liner 144, the structural support member 148 being positioned between portions of inner liner 144 and outer jacket 146. In some examples, outer jacket 146 may be positioned around structural support member 148 such that outer jacket 146 covers at least a part or all of both inner liner 144 and structural support member 148. Outer jacket 146, together with inner liner 144 and structural support member 148, may be configured to define elongated body 110 having the desired structural characteristics (e.g., flexibility, kink resistance, torque responsiveness, structural integrity, pushability, and column strength, which may be a measure of a maximum compressive load that can be applied to elongated body 110 without taking a permanent set). For example, outer jacket 146 may have stiffness characteristics that contribute to the desired stiffness profile of elongated body 110.

In some examples, outer jacket 146 may be formed using any suitable material including, but are not limited to, polymers, such as a polyether block amide (e.g., PEBAX®, commercially available from Arkema Group of Colombes, France), an aliphatic polyamide (e.g., Grilamid®, commercially available from EMS-Chemie of Sumter, S.C.), another thermoplastic elastomer (e.g., a thermoplastic or an elastomeric polymer), polyurethanes, polyamides, or other thermoplastic material, or combinations thereof.

In some examples, at least a portion of an outer surface of outer jacket 146 and/or inner member 118 includes one or more coatings, such as, but not limited to, an antithrombogenic coating, which may help reduce the formation of thrombi in vitro, an anti-microbial coating, and/or a lubricating coating.

Figure 4:
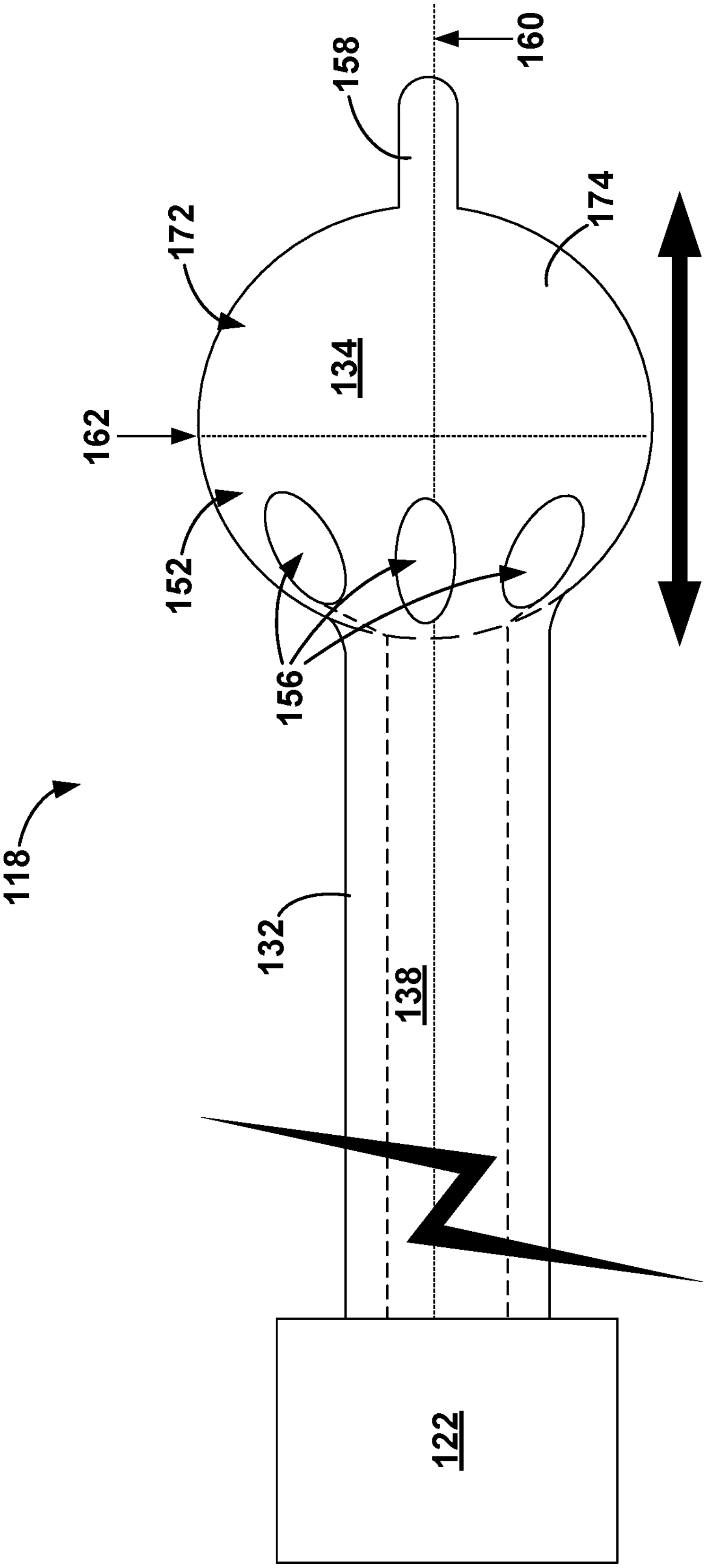
FIG. 4 is a conceptual side view of an example inner member of the catheter of FIG. 2.

Inner member 118 is configured to be disposed (e.g., introduced and positioned) within catheter lumen 140 of aspiration catheter 108, and deployed distally outward from distal opening 112 of catheter 108 during an aspiration procedure. FIG. 4 is a conceptual side view of an example inner member 118. Inner member 118 is configured to move proximally and distally relative to elongated body 110 of catheter 108 to contact and disrupt a thrombus (e.g., break-up the thrombus into smaller pieces and/or compress the thrombus into a smaller volume) to facilitate aspiration of the thrombus into catheter lumen 140 via distal opening 112. Additionally or alternatively, inner member 118 may be configured to move rotationally, e.g., about longitudinal axis 150, and/or in a direction transverse to longitudinal axis 150 (e.g., in a direction orthogonal to longitudinal axis 150).

As shown in FIG. 4, inner member 118 includes an elongated support structure 132 and a rigid member 134 (also referred to herein as a "noncompliant member 134") positioned at a distal portion of elongated support structure 132. Elongated support structure 132 may include a tubular structure, such as a braided polymer shaft or a hypotube (e.g., hypotube laser-cut to have desired flexibility characteristics), defining a support structure lumen 138 therein. At least a portion of rigid member 134 defines a cross-sectional dimension that is larger than a cross-sectional dimension of support structure 132, wherein the cross-sections are taken transverse or perpendicular to longitudinal axis 160.

Rigid member 134 is formed from a substantially rigid material, e.g., firm and/or non-compliant material, which is configured to resist deformation during contact with a thrombus. For example, in contrast to an expandable balloon or another expandable structure, rigid member 134 may have a fixed size. Thus, in some examples, rigid member 134 is configured to remain relatively the same size in catheter lumen 140, as well as outside of catheter lumen 140. While rigid member 134 may be formed from a material with some elasticity, such that rigid member 134 may compress slightly while in catheter lumen 140 in some examples, rigid member 134 is configured to maintain generally the same maximum cross-sectional dimension (e.g., a diameter) in a direction orthogonal to longitudinal axis 160, in catheter lumen 140 and when deployed out distal opening 112 of catheter 108. For example, a maximum cross-sectional dimension of rigid member 134 when in catheter lumen 140 can be within 10%, such as within 5% or even within 1%, of the maximum cross-sectional dimension when no external compressive forces are being applied to rigid member 134 by catheter 108 or the like.

Rigid member 134 includes an exterior surface 172 (also referred to herein as an outer surface) which, in some examples, may include an antithrombogenic coating, a lubricious coating, and/or one or more surface textures configured to help disrupt a thrombus. Exterior surface 172 includes proximal-facing surface 152, e.g., the portion of the exterior surface 172 facing catheter distal opening 112 when rigid member 134 is deployed from distal opening 112 and when at least part of support structure 132 is positioned within catheter lumen 140. For example, in examples in which rigid member 134 is generally spherical (e.g., spherical or nearly spherical to the extent permitted by manufacturing tolerances), proximal-facing surface 152 is the part of exterior surface 172 proximal to hemispherical plane 162.

Proximal-facing surface 152 defines one or more openings 156 defining respective fluid pathways between support structure lumen 138 and the exterior environment. In some examples, the only fluid-delivery openings defined by rigid member 134 are on proximal-facing surface 152 and not on distal-facing surface (on an opposite side of hemispherical plane 162 from surface 152 in the example shown in FIG. 4). By confining openings 156 to proximal-facing surface 152, inner member 118 is configured to direct a flow of a surgical fluid, such as saline, in a generally proximal direction in order to augment an applied proximal aspiration force. In addition, by confining openings 156 to proximal-facing surface 152 or confining fluid delivery in only the proximal direction, the fluid can direct a thrombus or thrombus segments towards catheter lumen 140 and suction force applied to catheter lumen 140 may help further draw the thrombus or thrombus segments into catheter lumen 140. In contrast, fluid flow in a distal direction (in a direction away from catheter lumen 140) may cause a thrombus or thrombus segments in a direction away from catheter lumen 140, which may result in a more inefficient (e.g., longer) medical aspiration procedure.

Openings 156 can be distributed along rigid member 134 in any suitable matter, such as evenly distributed about an outer perimeter of rigid member 134 (and in a direction extending about longitudinal axis 160) or unevenly distributed about the outer perimeter and/or longitudinally aligned along longitudinal axis 160 or having different longitudinal positions from at least one other opening 156.

Openings 156 may define any suitable geometric shape, including circular, oval, a quadrilateral shape, a tear drop shape (including sides tapering in a proximal or distal direction), an hourglass shape, or another suitable geometric shape. In some examples, openings 156 may also be configured or positioned along rigid member 134 to direct a fluid flow 168 (FIG. 5) in a particular direction. For instance, openings 156 may be oriented to direct the fluid flow proximally, e.g., along a line parallel to longitudinal axis 150 or within about 90 degrees of longitudinal axis 150. In other examples, openings 156 may be oriented so as to direct the fluid flow both proximally and radially inward or outward, as desired.

In addition to proximal-facing openings 156, in some examples, a distal-facing surface 174 of rigid member 134 may include one or more distal-facing openings (not shown). The distal-facing openings can be configured similarly to proximal-facing openings 156 in some examples, in shape, size, and/or distribution about rigid member 134.

In some examples, inner member 118 is configured to enable a user to selectively deliver fluid to one or more proximal-facing openings 156 (e.g., a subset of openings 156 or all of the openings) and, if present, to one or more distal-facing openings (e.g., a subset of the distal-facing openings or all of the distal-facing openings). For instance, a subset (e.g., one or more, but not all) or all of proximal-facing openings 156 can be fluidically coupled to a common fluid delivery lumen within elongated support structure 132 and, if inner member 118 includes one or more distal-facing openings, one or more a subset (e.g., one or more, but not all) or all of the distal-facing openings 156 can be fluidically coupled to a different fluid delivery lumen within elongated support structure 132.

Elongated support structure 132 can include any suitable number of lumens for the fluid delivery to one or more subsets of proximal-facing openings 156 and one or more subsets of the distal-facing openings. For example, in some examples, all of proximal-facing openings 156 are fluidically coupled to the same fluid delivery lumen. In other examples, a first subset of proximal-facing openings 156 are fluidically coupled to a first fluid delivery lumen and a second subset of proximal-facing openings 156 different from the first subset are fluidically coupled to a second fluid delivery lumen fluidically isolated from the first fluid delivery lumen. Similarly, if present, in all of the distal-facing openings can be fluidically coupled to the same fluid delivery lumen or a first subset of distal-facing openings can be fluidically coupled to one fluid delivery lumen and a second subset of distal-facing openings different from the first subset are fluidically coupled to a different fluid delivery lumen.

In examples in which elongated support structure 132 includes multiple fluid delivery lumens to enable selective delivery to different openings, system 100 includes an actuator (e.g., provided by a user interface coupled to control circuitry 128 or a switch) configured to enable the user to select the subset of fluid delivery openings for fluid delivery. For example, in response to receiving user input via the user interface, control circuitry 128 can actuate a valve (e.g., a multiple-way valve) to fluidically coupled fluid source 106 with the one or more lumens of support structure 132 corresponding to the openings indicated by the user input. As another example, a user may manually move a switch to fluidically couple fluid source 106 with the one or more lumens of support structure 132 corresponding to the fluid delivery openings to be used for fluid delivery. For example, the actuator can enable a user (e.g., a clinician) to select or alternate between a proximal-directed fluid flow from proximal-facing openings 156 and a distal-directed fluid flow from the distal-facing openings, to provide more control over the aspiration procedure. As another example, the actuator can enable a user to select only a subset of proximal-facing openings 156 or only a subset of distal facing openings for fluid delivery.

In the example shown in FIG. 4, rigid member 134 defines a substantially spherical shape. However, this example configuration of rigid member 134 is not intended to be limiting. Inner member 118 can have any suitable configuration for engaging and segmenting a thrombus within a patient's vasculature. For instance, in other examples, inner member 118 may include an oblong or "egg" shape, a shape defining substantially flat or planar proximal-facing and/or distal-facing surfaces (e.g., the planes oriented perpendicular to longitudinal axis 160, or any other suitable geometric three-dimensional shape.

Figure 5:
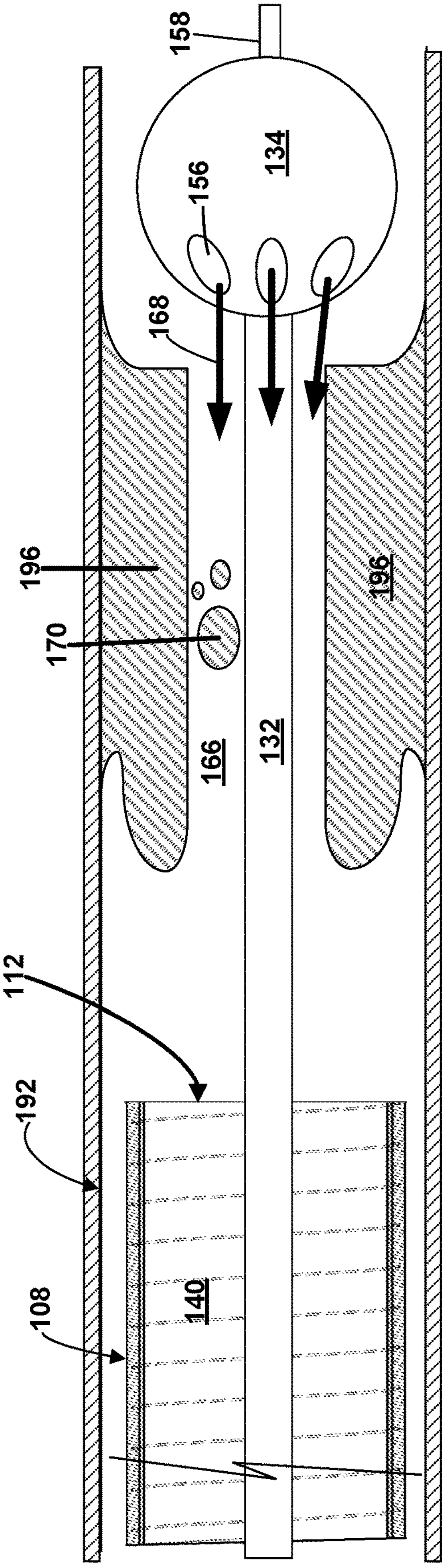
FIGS. 5 and 6 are conceptual cross-sectional views of another example of the distal portion of the catheter of FIG. 2 while introduced within vasculature of a patient, showing the inner member in a deployed configuration and a retracted configuration, respectively, where the cross-section is taken through a center of the catheter and along a longitudinal axis of the catheter.

As shown in FIG. 4, in some examples (but not all examples), a distal-most tip of inner member 118 includes an elongated element 158. Elongated element 158 may include a tapered distal portion of rigid member 134, a guidewire, or any other suitable structure configured to define a pathway through a thrombus and through which rigid member 134 can extend to penetrate through the thrombus to a distal side of the thrombus. An example of this "deployed" configuration of inner member 118 is illustrated in FIG. 5. In other examples, inner member 118 does not include elongated element 158. That is, inner member 118 terminates at a distal-most end of rigid member 134. In some of these examples, distal-facing surface 174 defines a substantially hemispherical shape.

FIG. 5 is a conceptual cross-sectional view of another example of the distal portion 124 of the catheter 108 of FIG. 2 while introduced within vasculature 192 of a patient with inner member 118 in a deployed configuration, in which rigid member 134 is positioned on a distal side of thrombus 196, opposite catheter 108, which is positioned on a proximal side of thrombus 196.

A clinician may position rigid member 134 of inner member 118 on a distal side of thrombus 196 using any suitable technique. In some examples, the clinician may manually distally advance inner member 118 through catheter lumen 140, distally out distal opening 112, and through thrombus 196 to position rigid member 134 on the distal side or within thrombus 196. In other examples, the clinician may actuate a user-input mechanism coupled to control circuitry 128 (FIG. 1) to cause motion-driving mechanism 122 (FIG. 4) to deploy rigid member 134 distally outward from distal opening 112 of catheter 108 and toward thrombus 196. As rigid member 134 contacts a proximal side of thrombus 196, elongated element 158 penetrates thrombus 196, forming a pathway 166 through thrombus 196 for rigid member 134. Rigid member 134 passes distally through pathway 166 and becomes located at a position that is distal to all or part of thrombus 196.

The clinician may control delivery of a fluid through openings 156. For example, the clinician may actuate an appropriate mechanism (e.g., a button, switch, pull wire, or the like) to cause aspiration fluid 168 (e.g., saline or blood)

to flow through support structure lumen 138 and out from openings 156. Because of the position of openings 156 on proximal-facing surface 152 of rigid member 134, the fluid flow 168 may proximally urge or bias thrombus portions toward distal opening 112 of catheter 108. Segmented portions 170 of thrombus 196 may be smaller parts of thrombus 196 that break off of thrombus 196 due to mechanical force from rigid member 134 moving through thrombus 196, the force of fluid flow 165, the use of mechanical thrombectomy device, aspiration force delivered via catheter lumen 140, or the like or any combination thereof. The segmented portions 170 of thrombus 196 may be aspirated proximally through catheter lumen 140 of catheter 108 and into discharge reservoir 104 (FIG. 1) via the suction force.

As described above, the proximal fluid flow 168 may provide an additional benefit by diluting and/or displacing an amount of patient fluid, such as blood, that might otherwise be incidentally aspirated during the procedure. For instance, the proximal-facing orientations of openings 156 are configured to cause proximal fluid flow 168 to be directed proximally, such that the fluid displaces and/or dilutes a volume of the patient's blood before it is aspirated through distal opening 112, into catheter lumen 140, and into discharge reservoir 104. Reducing incidental patient blood withdrawal in this manner is believed to improve patient outcomes, such as by reducing patient recovery time, and the like. In addition, in some cases, directing fluid in the proximal direction and not in a distal direction may also be beneficial because fluid delivered in a distal direction may have an intended effect of diverting material intended for aspiration away from distal opening 112 of catheter 108, and may in some cases interfere with efficient aspiration. However, as discussed above, in some examples, inner member 118 is configured to selectively enable fluid flow in a distal direction.

During or after the medical aspiration is complete, the clinician can proximally withdraw inner member 118 back into catheter lumen 140, e.g., manually or by actuating motion-driving mechanism 122. This proximal motion of inner member 118, such as when proximal-facing surface 152 contacts thrombus 196, can help urge thrombus 196 closer to distal catheter opening 112 for subsequent aspiration.

Figure 6:
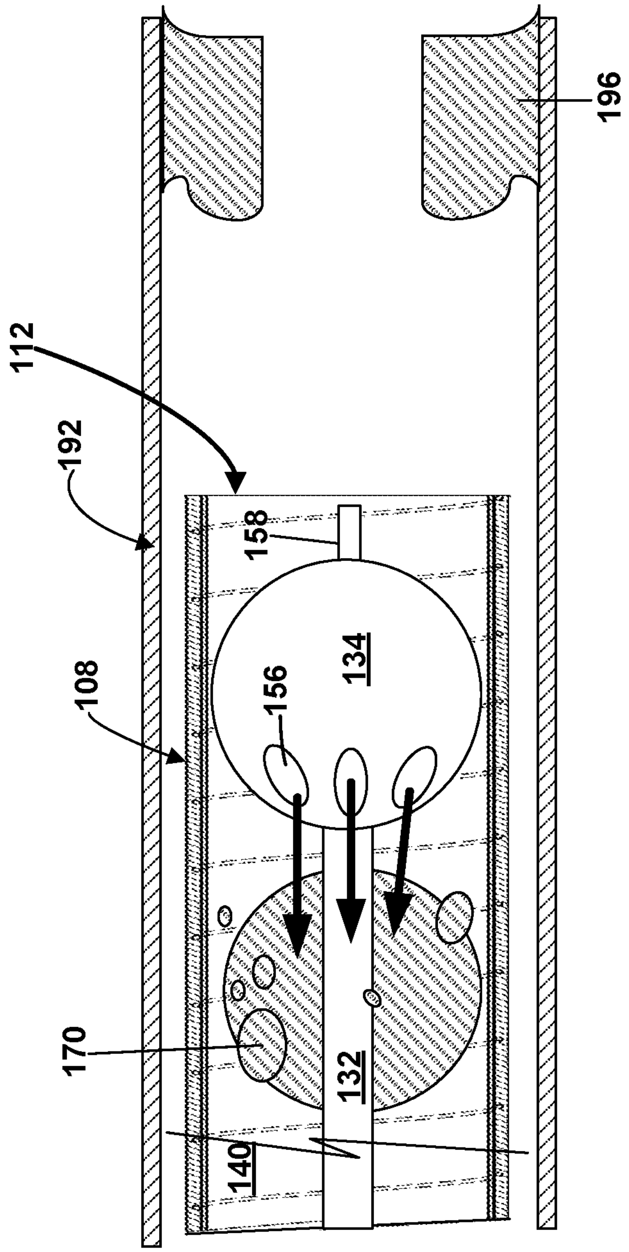

FIG. 6 is a conceptual cross-sectional view of another example of the distal portion 124 of the catheter 108 of FIG. 2 while introduced within vasculature 192 of a patient, showing the inner member 118 in a retracted configuration, where the cross-section is taken through a center of the catheter 108 and along a longitudinal axis 160 of the catheter 108. In the retracted configuration shown in FIG. 6, inner member 118 is fully positioned within catheter lumen 140. In this position of inner member 118 relative to catheter 108, the clinician may actuate the appropriate mechanism (e.g., a button, switch, pull wire, or the like) to deploy an additional proximal flow of aspiration fluid 168 out from openings 156.

Proximal fluid flow 168 is configured to clear or flush any remaining thrombus portions 170 that may have become lodged within catheter lumen 140, as necessary. The segmented thrombus portions 170 may be aspirated proximally through catheter lumen 140 of catheter 108 and into discharge reservoir 104 (FIG. 1) via an applied suction force. The configuration of inner member 118, including proximally oriented openings 156, enable this flushing to be performed during the aspiration procedure, e.g., without having to withdraw the medical system 100 from the patient's vasculature first. In this way, medical system 100 is configured to substantially reduce both an overall duration of the aspiration procedure, as well as to reduce a volume of patient fluid (e.g., blood, etc.) that would otherwise be incidentally withdrawn from the patient's vasculature.

With the catheter lumen 140 cleared, the clinician may re-deploy inner member 118 to forcefully contact and/or penetrate any remaining portions of thrombus 196 remaining within vasculature 192, and repeat this process as many times as needed to fully clear the thrombus 196. The clinician may then withdraw catheter 108 from vasculature 192.

Figure 7:
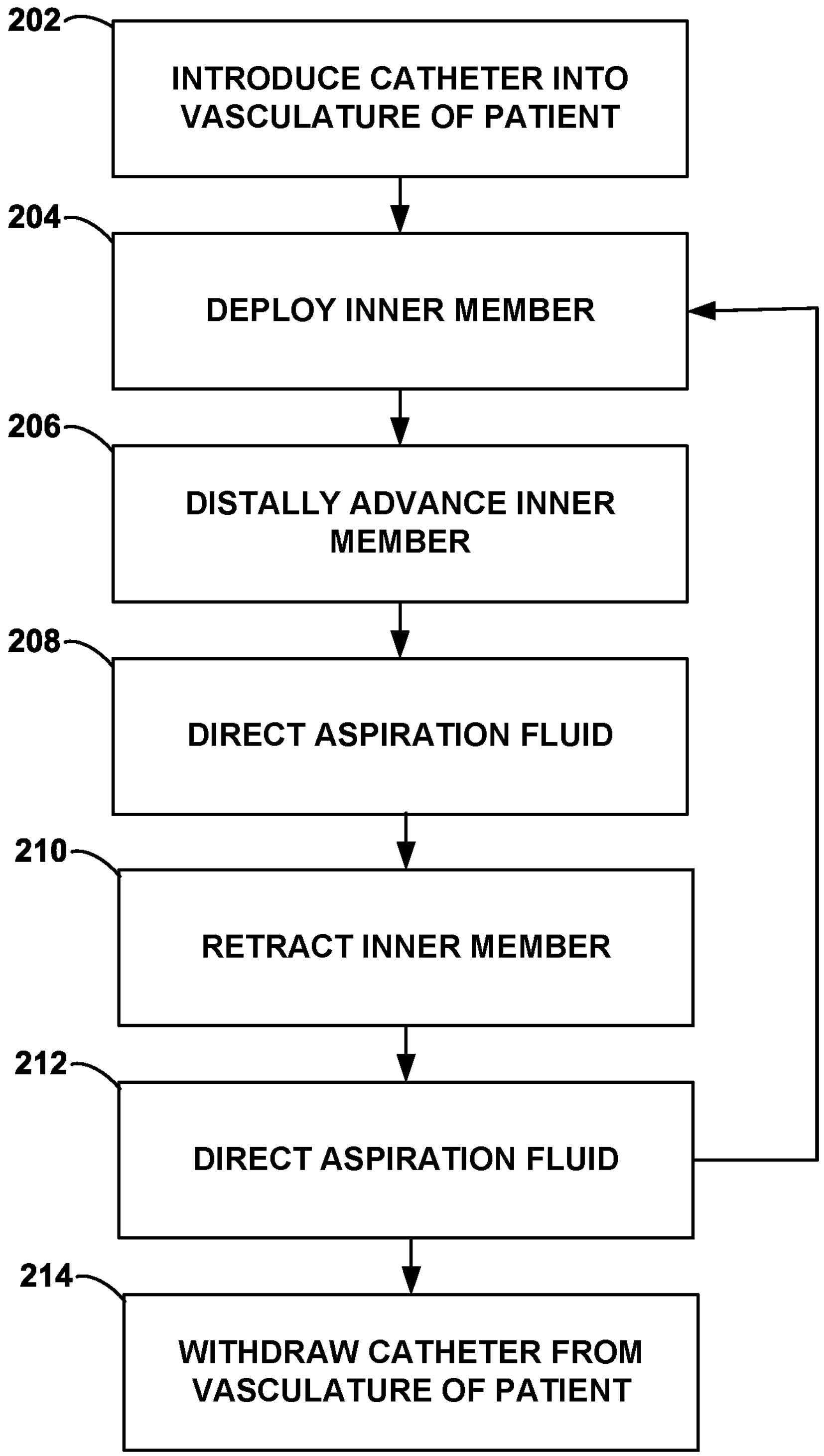
FIG. 7 is a flow diagram of an example method of using the medical aspiration system of FIG. 1.

FIG. 7 is a flow diagram of an example method of using catheter 108 of FIGS. 2 and 3. The techniques of FIG. 7 include introducing catheter 108 into vasculature of the patient (202), deploying inner member 118 from catheter lumen 140 and out distal opening 112 to contact and disrupt a thrombus while aspirating segmented thrombus portions through catheter 108 (204), distally advancing inner member 118 through the thrombus (206), directing a proximal fluid flow 168 from the inner member 118 to urge segmented thrombus portions toward the distal opening 112 of the catheter (208), retracting inner member 118 back into catheter lumen 140 of catheter 108 (210), directing another proximal fluid flow 168 from the inner member 118 to flush the catheter lumen 140 (212), and removing catheter 108 from the vasculature of the patient once the procedure is complete.

In some examples, inserting catheter 108 into vasculature of a patient (202) may include initially introducing a guidewire, guide catheter, or another guide member into the vasculature of the patient to a target treatment site. Elongated body 110 may then be introduced over the guidewire and advanced to the target treatment site. Additionally, or alternatively, catheter 108 may be introduced into vasculature of a patient with the aid of a guide catheter or sheath. For example, the guide catheter may be initially introduced into vasculature of a patient and positioned adjacent a target treatment site. Catheter 108 may then be introduced through an inner lumen of the guide catheter.

Inner member 118 may be deployed into the vasculature through catheter lumen 140 (204). In some cases, inner member 118 is positioned within catheter lumen 140 as catheter 108 is navigated to the target treatment site. In other examples, inner member 118 is introduced into catheter lumen 140 and navigated to the target treatment site through catheter lumen 140 after catheter 108 is navigated to the target treatment site. Additionally or alternatively, a guidewire may be advance to the target treatment site, and inner member 118 may be advanced to the treatment site along the guidewire (e.g., with the guidewire positioned inside an inner lumen of inner member 118).

In some examples, a clinician causes inner member 118 to be repeatedly distally deployed and proximally withdrawn to contact and disrupt the thrombus 196, e.g., to break the thrombus into smaller portions and/or to compress the thrombus or thrombus portions into smaller volumes. A suction force may be applied to catheter lumen 140 of catheter 108 to proximally withdraw the thrombus portions into distal opening 112 of catheter 108. For example, once distal portion 124 of catheter 108 is positioned proximate to a thrombus, a clinician may actuate a suction source 102 to apply a suction force to lumen 140. In some examples, the suction force applied to catheter lumen 140 of catheter 108 is varied over time, referring to herein as cyclical aspiration. As discussed above, during this cyclical aspiration, at least a portion of the thrombus may be pulled into contact with actuated inner member 118, thereby segmenting the thrombus into smaller pieces, which are then aspirated proximally through catheter lumen 140.

The technique of FIG. 7 also includes distally advancing inner member 118 through the thrombus until the rigid member 134 at the distal portion of inner member 118 is positioned on a distal side of the thrombus (206). An aspiration fluid, such as saline or the like, may be introduced into support structure lumen 138 and out proximal-facing openings 156 defined by rigid member 134 to urge segmented thrombus portions toward the distal catheter opening 112 for aspiration (208). In some examples, control circuitry 128 is configured to determine and coordinate a rate or volume of introduced aspiration fluid with a corresponding rate or volume of aspirated patient fluid, e.g., by actuating suction source 102, fluid source 106, and/or an electronic valve 120 coupled to aspiration tubing 114 and/or irrigation tubing 116. As one non-limiting example, control circuitry 128 may be configured to actuate suction source 102 and open valve 120 such that about one volume unit of aspiration fluid is introduced via inner member 118 for every two volume units of patient fluid aspirated into discharge reservoir 104 (e.g., a 50% aspiration fluid to patient fluid ratio). The particular ratio may be variably selected and controlled by a user. As another example, control circuitry 128 is configured to approximately balance the volumes of aspiration fluid introduced and patient fluid withdrawn, e.g., such that the volumes are approximately equal.

The technique of FIG. 7 also includes retracting inner member 118 back into catheter lumen 140 of catheter 108 (210) and directing another proximal fluid flow 168, as necessary, from the openings 156 on proximal-facing surface 152 of inner member 118 to flush the catheter lumen 140 (212). The previous steps may be repeated, e.g., until the thrombus has been cleared from the patient's vasculature, before removing catheter 108 may be removed from the vasculature of the patient (214).

The present disclosure includes the following non-limiting examples.

Example 1: A medical system including an aspiration catheter defining a catheter lumen; and an inner member configured to be received in the catheter lumen and extend distally outward from a distal opening of the catheter, wherein the inner member comprises: an elongated support structure configured to move axially within the catheter lumen; and a rigid member at a distal portion of the elongated support structure, wherein the rigid member defines a larger cross-sectional dimension than the elongated support structure, and wherein a proximal-facing surface of the rigid member defines one or more openings configured to deliver a fluid into vasculature of a patient to dilute or displace a volume of blood aspirated from the vasculature of the patient and through the catheter lumen.

Example 2: The medical system of example 1, wherein the rigid member of the inner member defines a generally spherical shape, and wherein the proximal-facing surface of the rigid member comprises a proximal hemispherical surface of the generally spherical shape.

Example 3: The medical system of example 1 or example 2, wherein the elongated support structure of the inner member comprises a tubular body defining a support structure lumen configured to receive the fluid, wherein the support structure lumen is fluidically coupled to the one or more openings of the rigid member.

Example 4: The medical system of any of examples 1-3, wherein the elongated support structure comprises a braided polymer shaft.

Example 5: The medical system of any of examples 1-3, wherein the elongated support structure comprises a hypotube.

Example 6: The medical system of any of examples 1--5, wherein the inner member further comprises an elongated element distal to the rigid member, the elongated element configured to form a pathway through the thrombus for the inner member.

Example 7: The medical system of example 6, wherein the elongated element comprises a guidewire.

Example 8: The medical system of any of examples 1-7, wherein the elongated support structure defines a support structure lumen, the medical system further includes an aspiration pump fluidically coupled to the catheter lumen; a fluid source fluidically coupled to the support structure lumen and configured to store the fluid; a valve fluidically coupled between the aspiration pump and the distal opening of the aspiration catheter; and control circuitry configured to control an opening and a closing of the valve to synchronize an aspiration force from the aspiration pump with a supply of the fluid from the fluid source.

Example 9: The medical system of example 8, further comprising an actuator switch coupled to the valve, wherein the control circuitry is configured to control the opening and the closing of the valve via the actuator switch.

Example 10: The medical system of any of examples 1-9, wherein an exterior surface of the rigid member comprises an antithrombogenic coating.

Example 11: The medical system of any of examples 1-10, wherein the rigid member is non-compliant.

Example 12: A method including distally advancing an aspiration catheter toward a thrombus at a target treatment site within vasculature of a patient, the aspiration catheter defining a catheter lumen; deploying a rigid member of an inner member from a distal opening of the catheter and distally through the thrombus, wherein the inner member comprises: an elongated support structure configured to move axially within the catheter lumen; and the rigid member at a distal portion of the elongated support structure, wherein the rigid member defines a larger cross-sectional dimension than the elongated support structure, and wherein a proximal-facing surface of the rigid member defines one or more openings; actuating a suction source to aspirate the thrombus into the catheter lumen via the distal opening of the catheter; and proximally introducing, via the one or more openings, a fluid into the vasculature of the patient to dilute or displace a volume of blood aspirated from the vasculature through the catheter lumen.

Example 13: The method of example 12, wherein the rigid member defines a generally spherical shape, and wherein the proximal-facing surface of the rigid member comprises a proximal hemispherical surface of the generally spherical shape.

Example 14: The method of example 12 or example 13, wherein the elongated support structure comprises a thin-walled tube defining a support structure lumen configured to receive the surgical fluid, wherein the support structure lumen is fluidically coupled to the one or more openings of the rigid member.

Example 15: The method of any of examples 12-14, wherein the elongated support structure comprises a braided polymer shaft.

Example 16: The method of any of examples 12-14, wherein the elongated support structure comprises a hypotube.

Example 17: The method of any of examples 12-16, further includes proximally withdrawing the inner member into the catheter lumen; and introducing the fluid into the lumen via the one or more openings on the proximal-facing surface of the rigid member.

Example 18: The method of example 17, wherein, while the inner member is positioned within the catheter lumen, the fluid is configured to flush the catheter lumen.

Example 19: The method of any of examples 12-18, wherein the inner member further comprises an elongated element distal to the rigid member, and wherein distally advancing the inner member out from the distal opening of the catheter comprises using the elongated element to form a pathway through the thrombus.

Example 20: The method of any of examples 12-19, further comprising controlling a valve coupled to the aspiration catheter to control a volume of the introduced fluid relative to the volume of blood aspirated from the vasculature through the catheter lumen.

Example 21: The method of example 20, wherein the volume of introduced fluid approximately equals the volume of blood aspirated.

Example 22: The method of any of examples 12-21, wherein the fluid is configured to proximally bias the thrombus toward the distal opening of the aspiration catheter.

Example 23: A medical system including an aspiration catheter defining a catheter lumen; and an inner member configured to be received in the catheter lumen and extend distally outward from a distal opening of the catheter, wherein the inner member comprises: an elongated support structure configured to move axially within the catheter lumen; and a noncompliant member at a distal portion of the elongated support structure, wherein the noncompliant member is enlarged relative to the elongated support structure, wherein the noncompliant member is configured to fit within the catheter lumen, and wherein a proximal-facing surface of the noncompliant member defines one or more openings configured to deliver a fluid into a vasculature of a patient to dilute or displace a volume of blood aspirated from the vasculature of the patient and through the catheter lumen.

Example 24: The medical system of example 23, wherein the elongated support structure defines a support structure lumen, the system further includes an aspiration pump fluidically coupled to the catheter lumen; a fluid source fluidically coupled to the support structure lumen and configured to store the fluid; a valve fluidically coupled between the aspiration pump and the distal opening of the aspiration catheter; and control circuitry configured to control an opening and a closing of the valve to synchronize an aspiration force from the aspiration pump with a supply of the fluid from the fluid source.

Various aspects of the disclosure have been described. These and other aspects are within the scope of the following claims.

What is claimed is:

1. A medical system comprising:

an aspiration catheter defining a catheter lumen; and an inner member configured to be received in the catheter lumen and extend distally outward from a distal opening of the aspiration catheter, wherein the inner member comprises:

an elongated support structure configured to move axially within the catheter lumen; and a rigid member at a distal portion of the elongated support structure, wherein the rigid member defines a larger cross-sectional dimension than the elongated support structure, and wherein a proximal-facing surface of the rigid member defines one or more openings configured to deliver a fluid into vasculature of a patient to dilute or displace a volume of blood aspirated from the vasculature of the patient and through the catheter lumen, wherein the rigid member defines an ellipsoidal shape, and wherein the proximal-facing surface of the rigid member comprises a proximal ellipsoidal surface of the ellipsoidal shape.

2. The medical system of claim 1, wherein the ellipsoidal shape of the rigid member of the inner member defines a generally spherical shape, and wherein the proximal- facing proximal ellipsoidal surface of the rigid member comprises a proximal hemispherical surface of the generally spherical shape.

3. The medical system of claim 1, wherein the elongated support structure comprises a tubular body defining a support structure lumen configured to receive the fluid, wherein the support structure lumen is fluidically coupled to the one or more openings of the rigid member.

4. The medical system of claim 1, wherein the elongated support structure comprises a braided polymer shaft.

5. The medical system of claim 1, wherein the elongated support structure comprises a hypotube.

6. The medical system of claim 1, wherein the inner member further comprises an elongated element distal to the rigid member, the elongated element configured to form a pathway through a thrombus for the inner member.

7. The medical system of claim 1, wherein the elongated support structure defines a support structure lumen, the medical system further comprising:

an aspiration pump fluidically coupled to the catheter lumen;

a fluid source fluidically coupled to the support structure lumen and configured to store the fluid;

a valve fluidically coupled between the aspiration pump and the distal opening of the aspiration catheter; and control circuitry configured to control an opening and a closing of the valve to synchronize an aspiration force from the aspiration pump with a supply of the fluid from the fluid source.

8. The medical system of claim 7, further comprising an actuator switch coupled to the valve, wherein the control circuitry is configured to control the opening and the closing of the valve via the actuator switch.

9. The medical system of claim 1, wherein an exterior surface of the rigid member comprises an antithrombogenic coating.

10. The medical system of claim 1, wherein the rigid member is non-compliant.

11. The medical system of claim 1, wherein the ellipsoidal shape of the rigid member comprises at least one of a spheroid shape or an oblong shape, and wherein the proximal ellipsoidal surface of the rigid member comprises a proximal-facing surface of the at least one of the spheroid shape or the oblong shape.

12. A method comprising:

distally advancing an aspiration catheter toward a thrombus at a target treatment site within vasculature of a patient, the aspiration catheter defining a catheter lumen;

deploying a rigid member of an inner member from a distal opening of the aspiration catheter and distally through the thrombus, wherein the inner member comprises:

an elongated support structure configured to move axially within the catheter lumen; and the rigid member at a distal portion of the elongated support structure, wherein the rigid member defines a larger cross-sectional dimension than the elongated support structure, and wherein a proximal-facing surface of the rigid member defines one or more openings, wherein the rigid member defines an ellipsoidal shape, and wherein the proximal-facing surface of the rigid member comprises a proximal ellipsoidal surface of the ellipsoidal shape;

actuating a suction source to aspirate the thrombus into the catheter lumen via the distal opening of the aspiration catheter; and proximally introducing, via the one or more openings, a fluid into the vasculature of the patient to dilute or displace a volume of blood aspirated from the vasculature through the catheter lumen.

13. The method of claim 12, wherein the ellipsoidal shape of the rigid member defines a generally spherical shape, and wherein the proximal-facing proximal ellipsoidal surface of the rigid member comprises a proximal hemispherical surface of the generally spherical shape.

14. The method of claim 12, wherein the elongated support structure comprises a thin-walled tube defining a support structure lumen configured to receive the fluid, wherein the support structure lumen is fluidically coupled to the one or more openings of the rigid member.

15. The method of claim 12, further comprising:

proximally withdrawing the inner member into the catheter lumen; and while the inner member is in the catheter lumen, introducing the fluid into the catheter lumen via the one or more openings on the proximal-facing surface of the rigid member.

16. The method of claim 12, wherein the inner member further comprises an elongated element distal to the rigid member, and wherein distally advancing the inner member out from the distal opening of the aspiration catheter comprises using the elongated element to form a pathway through the thrombus.

17. The method of claim 12, further comprising controlling a valve coupled to the aspiration catheter to control a volume of the introduced fluid relative to the volume of blood aspirated from the vasculature through the catheter lumen.

18. The method of claim 17, wherein the volume of introduced fluid approximately equals the volume of blood aspirated.

19. The method of claim 12, wherein the fluid is configured to proximally bias the thrombus toward the distal opening of the aspiration catheter.

20. A medical system comprising:

an aspiration catheter defining a catheter lumen; and an inner member configured to be received in the catheter lumen and extend distally outward from a distal opening of the aspiration catheter, wherein the inner member comprises:

an elongated support structure configured to move axially within the catheter lumen; and a noncompliant member at a distal portion of the elongated support structure, wherein the noncompliant member is enlarged relative to the elongated support structure, wherein the noncompliant member is configured to fit within the catheter lumen, and wherein a proximal-facing surface of the noncompliant member defines one or more openings configured to deliver a fluid into a vasculature of a patient to dilute or displace a volume of blood aspirated from the vasculature of the patient and through the catheter lumen, wherein the noncompliant member defines an ellipsoidal shape, and wherein the proximal-facing surface of the noncompliant member comprises a proximal ellipsoidal surface of the ellipsoidal shape.

21. The medical system of claim 20, wherein the elongated support structure defines a support structure lumen, the medical system further comprising:

an aspiration pump fluidically coupled to the catheter lumen;

a fluid source fluidically coupled to the support structure lumen and configured to store the fluid;

a valve fluidically coupled between the aspiration pump and the distal opening of the aspiration catheter; and control circuitry configured to control an opening and a closing of the valve to synchronize an aspiration force from the aspiration pump with a supply of the fluid from the fluid source.

22. The medical system of claim 11, wherein the oblong shape comprises an egg shape.

* * * * *